(12) United States Patent
Bock et al.

(10) Patent No.: US 9,353,012 B2
(45) Date of Patent: May 31, 2016

(54) CHARGE-COMPENSATING DOPANT STABILIZED ALUMINA-ZIRCONIA CERAMIC MATERIALS AND RELATED MATERIALS, APPARATUS, AND METHODS

(71) Applicant: Amedica Corporation, Salt Lake City, UT (US)

(72) Inventors: Ryan M. Bock, Salt Lake City, UT (US); Bryan J. McEntire, Sandy, UT (US); Ramaswamy Lakshminarayanan, West Jordan, UT (US)

(73) Assignee: Amedica Corporation, Salt Lake City, UT (US)

( * ) Notice: Subject to any disclaimer, the term of this patent is extended or adjusted under 35 U.S.C. 154(b) by 136 days.

(21) Appl. No.: 14/216,952

(22) Filed: Mar. 17, 2014

(65) Prior Publication Data
US 2014/0265065 A1    Sep. 18, 2014

Related U.S. Application Data

(60) Provisional application No. 61/798,431, filed on Mar. 15, 2013.

(51) Int. Cl.
*C04B 35/119* (2006.01)
*C04B 35/505* (2006.01)
(Continued)

(52) U.S. Cl.
CPC .............. *C04B 35/505* (2013.01); *A61L 27/10* (2013.01); *A61L 27/105* (2013.01); *C04B 35/117* (2013.01); *C04B 35/119* (2013.01); *C04B 35/44* (2013.01); *C04B 35/62685* (2013.01); *C04B 35/64* (2013.01); *C04B 35/6455* (2013.01); *A61L 2430/24* (2013.01); *C04B 2235/3206* (2013.01);
(Continued)

(58) Field of Classification Search
CPC ............ C04B 35/19; C04B 2235/3225; C04B 2235/3224; C04B 2235/3251; C04B 2235/32461; A61L 27/105
See application file for complete search history.

(56) References Cited

U.S. PATENT DOCUMENTS 4,298,385 A    11/1981  Claussen et al.
4,316,964 A    2/1982   Lange
(Continued)

OTHER PUBLICATIONS

B.C. Yu, et. al., "Colloidal Isopressing: A New Shape-Forming Method," 13, 4, 276-280. (2001).
(Continued)

*Primary Examiner* — Erin Snelting
(74) *Attorney, Agent, or Firm* — Phillips Ryther & Winchester; Matthew D. Thayne

(57) ABSTRACT

Ceramic materials comprising charge-compensating dopants and related methods. In some embodiments, the materials may comprise dopants such as $Y_2O_3$, $Gd_2O_3$, $Nb_2O_5$, and/or $Ta_2O_5$. Some embodiments may comprise a molar concentration of $Y_2O_3$ and/or $Gd_2O_3$ that is at least approximately equal to the molar concentration of $Nb_2O_5$ and/or $Ta_2O_5$. Certain embodiments and implementations may comprise particular, unique concentrations or concentration ranges of various compounds/materials in order to improve performance for use of such ceramic materials as biomedical implants.

22 Claims, 2 Drawing Sheets

(51) Int. Cl.

| | |
|---|---|
| C04B 35/64 | (2006.01) |
| C04B 35/117 | (2006.01) |
| C04B 35/44 | (2006.01) |
| C04B 35/626 | (2006.01) |
| C04B 35/645 | (2006.01) |
| A61L 27/10 | (2006.01) |

(52) U.S. Cl.
CPC . *C04B 2235/3208* (2013.01); *C04B 2235/3213* (2013.01); *C04B 2235/3217* (2013.01); *C04B 2235/3222* (2013.01); *C04B 2235/3224* (2013.01); *C04B 2235/3225* (2013.01); *C04B 2235/3229* (2013.01); *C04B 2235/3232* (2013.01); *C04B 2235/3244* (2013.01); *C04B 2235/3251* (2013.01); *C04B 2235/96* (2013.01)

(56) References Cited

U.S. PATENT DOCUMENTS

| | | | |
|---|---|---|---|
| 5,002,911 | A | 3/1991 | Matsumoto et al. |
| 5,830,816 | A | 11/1998 | Burger et al. |
| 6,387,132 | B1 | 5/2002 | Deppisch et al. |
| 6,452,957 | B1 | 9/2002 | Burger et al. |
| 6,787,080 | B1 | 9/2004 | Lange et al. |
| 7,012,036 | B2 | 3/2006 | Nawa et al. |
| 7,037,603 | B2 | 5/2006 | Lasater |
| 7,056,851 | B2 | 6/2006 | Nawa |
| 7,148,167 | B2 | 12/2006 | Shikata et al. |
| 7,297,420 | B2 | 11/2007 | Jiang |
| 7,435,443 | B2 | 10/2008 | Jiang |
| 7,820,577 | B2 | 10/2010 | Shikata et al. |
| 7,928,028 | B2 | 4/2011 | Nawa et al. |
| 8,093,168 | B2 | 1/2012 | Nawa et al. |
| 2002/0010070 | A1 | 1/2002 | Cales et al. |
| 2004/0152034 | A1* | 8/2004 | Cummings ......... A61K 6/0276 433/8 |
| 2006/0046070 | A1 | 3/2006 | Jiang |
| 2006/0121206 | A1 | 6/2006 | Jiang |
| 2008/0118722 | A1* | 5/2008 | Shikata ................ C04B 35/119 428/212 |

OTHER PUBLICATIONS

M. Hirano, et. al.,"Hydrothermal Stability of Yttria- and Ceria-doped Tetragonal Zirconia—Alumina Composites," J. Mat. Sci., 26, 5047-5052, (1991).

M. Hirano, et. al., "Strength and Phase Stability of Yttria-Ceria-Doped Tetragonal Zirconia/Alumina Composites Sintered and Hot Isostatically Pressed in Argon—Oxygen Gas Atmosphere," J. Am. Ceram. Soc., 74, [3], 606-11, (1991 ).

M. Hirano, et. al., "Fracture Toughness, Strength and Vickers Hardness of Yttria-Ceria-Doped Tetragonal Zirconia/Alumina Composites Fabricated by Hot Isostatic Pressing," J. Mat. Sci., 27, 3511-3518, (1992).

R. A. Cutler, et. al., "High Toughness Ce-TZP/Al2O3 Ceramics with Improved Hardness and Strength," J. Am. Ceram. Soc., 74, [1], 179-86, (1991).

S. Deville, et. al., "Low Temperature Ageing of Zirconia-Toughened Alumina Ceramics and its Implication in Biomedical Implants," J. Eur. Ceram. Soc., 23, 2975-2982, (2003).

T. Sato, et. al., "Postsintering Hot Isostatic Pressing of Ceria-Doped Tetragonal Zirconia/Alumina Composites in an Argon—Oxygen Gas Atmosphere," J. Am. Ceram. Soc., 72, [5], 761-64, (1989).

M. Nawa, et. al., "Tough and Strong Ce-TZP/Alumina Nanocomposties Doped with Titania," Ceramics International, 24,497-506, (1998).

Y. Shen, et. al., "Resistance to Low-Temperature Degradation of Equimolar YO1.5-TaO2.5 Stabilized Tetragonal ZrO2 Ceramics in Air," J Am Ceram Soc, 93, [7], 2024-2027, (2010).

ISO/DIS 6474-2.2—"Implants for surgery—Ceramic materials—Part 2: Composite materials based on a high purity alumina matrix with zirconia reinforcement," (2011 ).

O. Kruse, et. al., Characterization of H2O-aged TZP by elastic recoil detection analysis (ERDA). In Science and Technoilogy of Zirconia V, ed. S. Badwal, M. Bannister and R. Hannink. Technomic Publishing, Lancester, Basel, pp. 163-179.

F. Pitek, et. al., "Opportunities for TBCs in the ZrO2-YO1.5-TaO2.5 System," Surf Coat Tech, 201, 6044-6050, (2007).

H. Schubert, et. al., "Stability of Y-TZP During Hydrothermal Treatment: Neutron Experiments and Stability Considerations," J Euro Ceram Soc, [25], 1597-1602, (2005).

T. Duong, et. al., " Diffusion of Water Species in Yttria-Stabilized Zirconia," J Am Ceram Soc, 92, [11], 2731-2737, (2009).

Li, et al, "Effect of Dopants on Zirconia Stabilization—An X-ray Absorption Study: III, Charge-Compensating Dopants," J Am Ceram Soc, 77, [5], 1289-95, (1994).

D. J. Kim, et. al., "Phase Stability and Physical Properties of Cubic and Tetragonal ZrO2 in the System ZrO2,—Y2O3—Ta2O5," J. Am. Ceram. Soc., 74, 3061-65 (1991).

Kim, Effect of Ta2O5, Nb2O5, and HfO2 Alloying on the transformability of Stabilized Tetragonal ZrO2, J Am Ceram Soc, 73, [1], 115-120, (1990).

M. N. Rahaman, et al., Ceramics for Prosthetic Hip and Knee Joint Replacement, J. Am. Ceram. Soc., 90, [7], 1965-1988, (2007).

B. Sonny Bal, et al. "Ceramic Materials in Total Joint Arthroplasty," Semin Arthro 17:94-101 ' (2006).

W. Rieger, "Ceramics in Orthopedics—30 Years of Evolution and Experience," in: C. Rieker, S. Oberholzer and U. Wyss, World Triboloqy Forum in Arthroplasty, Published by Hans Huber, Bern, Switzerland, 3-14, (2001 ).

I. C. Clarke, et al., "Structural Ceramics in Orthopedics," in Bone Implant Interface, Edited by H. U. Cameron, 203-252, (St. Louis: Mosby Press, 1994).

J. Charnley, "Arthroplasty of the Hip: A New Operation," Lancet, 1, [7187], 1129-32, (1961 ).

K.Tanaka, et. al., "Ce-TZP/Al2O3 Nanocomposite as a Bearing Material in Total Joint Replacement," J Biomed Mater Res (Appl Biomater) 63: 262-270, (2002).

N. Sugano, et. al., "Polyethylene Sockets and Alumina Ceramic Heads in Cemented Total Hip Arthroplasty, A Ten-Year Study," J. Bone & Joint Surg., 77-B, 548-56, (1995).

S. B. Murphy, et. al., "Two- to 9-Year Clinical Results of Alumina Ceramic-on-Ceramic THA," Clinical Orthopaedics and Related Research, [453], 97-102, (2006).

Standard Specification for High-Purity Dense Aluminum Oxide for Medical Applications, ASTM F 603-00, (West Conshohocken, PA: ASTM Press).

C. Piconi, et. al., Alumina and Zirconia Ceramics in Joint Replacements, J. App. Biomater. & Biomech. , 1, 19-32, (2003).

R. S. Roy, et. al., "Sliding Wear Behavior of Submicron-Grained Alumina in Biological Environment," Published online Mar. 16, 2007; www.interscience.wiley.com; DOI: 10.1002/jbm.a.31230.

K-H. Koo, et. al., "Isolated Fracture of the Ceramic Head after Third Generation Alumina-on-Alumina Total Hip Arthroplasty," J. Bone Joint Surg. Am., (2008), 90:329-336; doi:10.2106/JBJS.F.01489.

J. Garino, et. al., The Reliability of Modern Alumina Bearings in Total Hip Arthroplasty, Semin. Arthro. 17,113-119, (2006).

R. C. Garvie, et. al., "Biocompatibility of Magnesia-Partially Stabilized Zirconia (Mg-PSZ) Ceramics," J. Mater. Sci., 19, [10], 3224-28, (1984).

T. Masaki, "Mechanical Properties of Toughened Zr02-Y2O3 Ceramics," J. Am. Ceram. Soc., 69, [8], 638-40, (1986).

B. Cales, "Zirconia Ceramic for Improved Hip Prosthesis—A Review," in: 6lh Biomaterial Symposium, Ceramic Implant Materials in Orthopaedic Surgery, 2-71, (Gottingen, Germany, 1994).

C. B. Rieker, et al., "Wear Behaviour of New Generation Ceramics," in: Ceramics in Orthopaedics, 8lh Biolox Symposium Proceedings, H. Zippel and M. Dietrich, Eds., 19-24, (Darmstadt: Steinkopff Verlag, 2003).

M. J. Kraay, et. al., "Zirconia versus Co—Cr Femoral Heads in Total Hip Arthroplasty," Clinical Orth. & Related Res., 453, 86-90, (2006).

R. H. J. Hannink, et. al., "Transformation Toughening in Zirconia-Containing Ceramics," J. Am. Ceram. Soc., 83, [3], 461-87, (2000).

(56) References Cited

OTHER PUBLICATIONS

Standard Specification for High-Purity Dense Magnesia Partially Stabilized Zirconia (Mg-PSZ) for Surgical Implant Applications, ASTM F2393-10, (West Conshohocken, PA: ASTM Press).

Standard Specification for High-Purity Dense Yttria Tetragonal Zirconium Oxide Polycrystal (Y-TZP) for Surgical Implant Applications, ASTM F1873-98, Withdrawn 2007, (West Conshohocken, PA: ASTM Press).

J. Chevalier, et. al., "The Tetragonal-Monoclinic Transformation in Zirconia: Lessons Learned and Future Trends," J. Am. Ceram. Soc., 92, [9], 1901-1920, (2009).

E. M. Santos, et. al., "Examination of Surface and Material Properties of Explanted Zirconia Femoral Heads," J. Arthroplasty, 19, [7], Suppl. 2, 30-34, (2004).

G. Maccauro, et. al., "Fracture of a Y-TZP Ceramic Femoral Head," J. Bone Joint Surg., 86, 1192-6, (2004), doi:10.1302/0301-620X. 86B8.

S. Hori, et. al., "Strength-Toughness Relations in Sintered and Isostatically Hot-Pressed ZrO2-Toughened Al2O3," J. Am. Ceram. Soc., 69, [3], 169-72, (1986).

G. Magnani, et.al., "Effect of the Composition and Sintering Process on Mechanical Properties and Residual Stresses in Zirconia-Alumina Composites," J. Eur. Ceram. Soc., 25, 3383-3392, (2005).

See Metoxit Zirconia Data Sheet, http://www.metoxit.com/english/downloads/mat_zr_e.pdf.

M. Kuntz, et. al., "Controlled Zirconia Phase Transformation in BIOLOX delta—a Feature of Safety," in Bioceramics and Alternative Bearings in Joint Arthroplasty, 10th Biolox Symposium Proceedings, 79-83, (Darmstadt, Steinkopff Verlag Press, 2005).

G. Willmann, et. al., "Biocompatibility of a New Alumina Matrix Biocomposite AMC," Proceedings of the 131h Int. Symp. on Ceramics in Medicine, Bologna, Italy, Nov. 22-26, 2000, pp. 569-572, (Switzerland: Trans Tech Publications, 2001).

H. Kamiya, et. al., "Erosion Wear Properties of Tetragonal ZrO2—(Y2O3)-Toughened Al2O3 Composites," J. Am. Ceram. Soc., 77, [3], 666-72, (1994).

B. Kerkwijk, et. al., "Processing of Homogeneous Zirconia-Toughened Alumina Ceramics with High Dry-Sliding Wear Resistance," J. Am. Ceram. Soc., 82, [8], 2087-93, (1999).

G. M. Insley, et. al., "In-Vitro Testing and Validation of Zirconia Toughened Alumina (ZTA)," in: Bioceramics in Joint Arthroplasty, 26-31, Proceedings of the ih Int. Biolox Symposium, Mar. 15-16, 2002, J.P. Garino and G. Willmann, Eds., (Stuttgart: Georg Thieme Verlag, 2002).

I.C. Clarke, et al., "Severe Simulation Test for Run-In Wear of All Alumina Compared to Alumina Composite THR," in: 10th Biolox Symposium Proceedings, 11-20, (Darmstadt, Steinkopff Verlag Press, 2005).

I. C. Clarke, et. al., "US Perspective on Hip Simulator Wear Testing of Biolox Delta in 'Severe' Test Modes," in: Ceramics in Orthopaedics, 11th Biolox Symposium Proceedings, Jun. 30-Jul. 1, 2006, F. Benazzo, F. Falez and M. Dietrich, Eds., (Darmstadt, Steinkopff Verlag, 2006).

I. C. Clarke, et. al., "Hip Simulator Wear Studies of an Alumina-Matrix Composite (AMC) Ceramic Compared to Retrieval Studies of AMC Balls with 1-7 Years Follow-Up," Wear, 267, 702-709, (2009).

G. Pezzotti, et. al., "Raman Spectroscopic Analysis of Advanced Ceramic Composite for Hip Prosthesis," J. Am. Ceram. Soc., 91, [4], 1199-1206, (2008).

G. Pezzotti, et. al., "Fracture Toughness Analysis of Advanced Ceramic Composite for Hip Prosthesis," J. Am. Ceram. Soc., 92, [8], 1817-1822, (2009).

J. Chevalier, et. al, "On the Kinetics and Impact of Tetragonal to Monoclinic Transformation in an Alumina/Zirconia Composite for Arthroplasty Applications," Biomaterials, 30, 5279-82, (2009).

G. Pezzotti, et. al., "Nano-Scale Topography of Bearing Surface in Advanced Alumina/Zirconia Hip Joint Before and After Severe Exposure in Water Vapor Environment," J. Orthop. Res., 28, 762-766 (2010).

G. Pezzotti, et. al., "Surface Topology of Advanced Alumina/Zirconia Composite Femoral Head as Compared with Commercial Femoral Heads Made of Monolithic Zirconia," J. Am. Ceram. Soc., 94, [3], 945-950, (2011).

M. Kuntz, "Validation of a New High Performance Alumina Matrix Composite for use in Total Joint Replacement," Semin. Arthro. 17, 141-145, (2006).

I. Papageorgiou, et. al., "The Effect of Nano- and Micron-Sized Particles of Cobalt—Chromium Alloy on Human Fibroblasts In Vitro," Biomaterials, 28, 2946-2958, (2007).

S. K. Hwang, et. al., "Fracture-Dissociation of Ceramic Liner," Orthopedics, 31, [8], 804.

W.G. Hamilton, et. al., "THA With Delta Ceramic on Ceramic: Results of a Multicenter Investigational Device Exemption Trial," C/in. Orthop. Relat. Res.; 468, [2], 358-366, (2010).

A. V. Lombardi, et. al., "Delta Ceramic-on-Alumina Ceramic Articulation in Primary THA," C/in. Orthop. Relat. Res.; 468, [2], 367-374, (2010).

V. Lughi, et. al., "Low Temperature Degradation-Aging-of Zirconia: A Critical Review of the Relevant Aspects in Dentistry," Dental Materials, 26, 807-820, (201 0).

C. Pecharroman, et. al., "Percolative Mechanism of Aging in Zirconia Containing Ceramics for Medical Applications," Adv. Mater., 15, [6], 507-11, (2003).

N. Claussen, "Fracture Toughness of Al2O3 with Unstabilized ZrO2 Dispersed Phase," J. Am. Ceram. Soc., 59, [1-2], 49-51, (1976).

* cited by examiner

CHARGE-COMPENSATING DOPANT STABILIZED ALUMINA-ZIRCONIA CERAMIC MATERIALS AND RELATED MATERIALS, APPARATUS, AND METHODS

RELATED APPLICATIONS

This application claims the benefit under 35 U.S.C. §119(e) of U.S. Provisional Patent Application No. 61/798,431 filed Mar. 15, 2013 and titled "CHARGE-COMPENSATING DOPANT STABILIZED ALUMINA-ZIRCONIA CERAMIC IMPLANTS AND RELATED MATERIALS, APPARATUS, AND METHODS," which application is incorporated herein by reference in its entirety.

SUMMARY

Disclosed herein are embodiments of apparatus, methods, and systems relating to ceramic materials comprising charge-compensating dopants, and related apparatus and methods, such as methods for manufacturing ceramic biomedical implants.

In a first example of an implementation of a method according to the invention, a first feedstock may be prepared by mixing ingredients comprising at least aluminum oxide and strontium carbonate or ingredients selected to yield aluminum oxide and strontium carbonate. A second feedstock may be prepared by mixing ingredients comprising at least aluminum oxide and calcium carbonate or ingredients selected to yield aluminum oxide and calcium carbonate. A slurry may then be prepared comprising materials from the first feedstock, materials from the second feedstock, and further comprising one or more trivalent dopants comprising at least one of yttrium oxide and gadolinium oxide, and one or more pentavalent dopants comprising at least one of tantalum pentoxide and niobium pentoxide.

In some embodiments and implementations, the one or more trivalent dopants may comprise any cation with a stable oxidation state of +3 and having an ionic radius between that of lutetium 3+ and that of praseodymium 3+. Thus, for example, in some embodiments and implementations, neodymium, yttrium, and/or gadolinium may be used as a trivalent dopant.

Similarly, in some embodiments and implementations, the one or more pentavalent dopants may comprise any cation with a stable oxidation state of +5 and an ionic radius between that of vanadium and niobium/tantalum. Thus, for example, in some embodiments and implementations, tantalum, niobium, and/or vanadium may be used as a pentavalent dopant.

Preferably, the one or more trivalent dopants are within at least about 0.5 mol % of the one or more pentavalent dopants. In some implementations, the trivalent dopant(s) may have the same, or at least substantially the same, molar concentration as the pentavalent dopant(s).

The slurry may additionally comprise one or more additional ingredients comprising or configured to yield at least a portion of a ceramic biomedical implant comprising at least zirconium dioxide, aluminum oxide, at least one of yttrium oxide and gadolinium oxide, and at least one of tantalum pentoxide and niobium pentoxide. Preferably, the one or more trivalent dopants comprise between about 1.5 mol % and about 6.5 mol % based on the total molar amounts of zirconium dioxide, cerium oxide, yttrium oxide, gadolinium oxide, tantalum pentoxide, and niobium pentoxide in the at least a portion of the ceramic biomedical implant, and, similarly, the one or more pentavalent dopants comprise between about 1.5 mol % and about 6.5 mol % based on the total molar amounts of zirconium dioxide, cerium oxide, yttrium oxide, gadolinium oxide, tantalum pentoxide, and niobium pentoxide in the at least a portion of the ceramic biomedical implant. In some such embodiments and implementations, the one or more trivalent dopants comprise between about 3.0 mol % and about 5.0 mol % based on the total molar amounts of zirconium dioxide, cerium oxide, yttrium oxide, gadolinium oxide, tantalum pentoxide, and niobium pentoxide in the at least a portion of the ceramic biomedical implant, and, similarly, the one or more pentavalent dopants comprise between about 3.0 mol % and about 5.0 mol % based on the total molar amounts of zirconium dioxide, cerium oxide, yttrium oxide, gadolinium oxide, tantalum pentoxide, and niobium pentoxide in the at least a portion of the ceramic biomedical implant.

In some embodiments and implementations, the one or more additional ingredients may further comprise a tetravalent dopant, such as cerium oxide. Thus, cerium oxide (or another tetravalent dopant) should be considered optional, but may provide benefits for certain applications. Use of such dopants may, for some embodiments and implementations, be used to reduce the amount of trivalent and/or pentavalent dopants. However, use of such a dopant in place of trivalent and/or pentavalent compounds may be less desirable for certain applications.

In embodiments and implementations comprising cerium oxide or another tetravalent dopant, such dopant may comprise no more than about 3.0% by mole based on the total molar amounts in the at least a portion of the ceramic biomedical implant. This may be preferable in implementation in which the isopressing process is performed in a reducing atmosphere (such as nitrogen gas). However, if argon gas or another non-reducing atmosphere is used during this process, the cerium oxide or another tetravalent dopant may comprise no more than about 10% by mole based on the total molar amounts in the at least a portion of the ceramic biomedical implant.

In some embodiments and implementations, the at least a portion of the ceramic biomedical implant may further comprise at least strontium oxide, magnesium oxide, titanium dioxide, and calcium oxide. In some such embodiments and implementations, at least a portion of the ceramic biomedical implant may comprise a combination of aluminum oxide, strontium oxide, magnesium oxide, titanium dioxide, and calcium oxide in a concentration of at least about 84% by volume.

In some embodiments and implementations, the at least a portion of the ceramic biomedical implant may comprise aluminum oxide in a concentration of at least about 74% by weight. In some such embodiments and implementations, the at least a portion of the ceramic biomedical implant may comprise aluminum oxide in a concentration of at least about 74.6% by weight.

In another example of an implementation of the invention for manufacturing a ceramic piece, the method may comprise preparing a slurry comprising, or comprising ingredients configured to yield a ceramic piece comprising, at least: aluminum oxide; zirconium dioxide; one or more trivalent dopants comprising at least one of yttrium oxide and gadolinium oxide; and one or more pentavalent dopants comprising at least one of tantalum pentoxide and niobium pentoxide. Preferably, the one or more trivalent dopants are within at least about 0.5 mol % of the one or more pentavalent dopants. As mentioned above, in some embodiments and implementations, the one or more trivalent dopants may be at least substantially identical (from a molar concentration standpoint) as the one or more pentavalent dopants.

A compact may be prepared that is derived from the slurry. For example, in some implementations, the slurry may be dried and then compressed to form a compact. Alternatively, the slurry may be compressed to form a compact and then dried.

The compact may be fired to obtain a fired ceramic piece comprising zirconium dioxide. In some embodiments and implementations, the zirconium dioxide may be in a concentration of between about 21% and about 24% by weight of the fired ceramic piece.

In some embodiments and implementations, the one or more trivalent dopants may comprise between about 1.5 mol % and about 6.5 mol % based on the total molar amounts of zirconium dioxide, cerium oxide, yttrium oxide, gadolinium oxide, tantalum pentoxide, and niobium pentoxide in the at least a portion of the ceramic biomedical implant. Similarly, the one or more pentavalent dopants may comprise between about 1.5 mol % and about 6.5 mol % based on the total molar amounts of zirconium dioxide, cerium oxide, yttrium oxide, gadolinium oxide, tantalum pentoxide, and niobium pentoxide in the at least a portion of the ceramic biomedical implant.

In embodiments and implementations in which the one or more trivalent dopants comprise only yttrium oxide, the yttrium oxide may comprise between about 3.25 mol % and about 4.75 mol % based on the total molar amounts of zirconium dioxide, cerium oxide, yttrium oxide, tantalum pentoxide, and niobium pentoxide in the at least a portion of the ceramic biomedical implant.

In other embodiments and implementations in which the one or more trivalent dopants comprise only gadolinium oxide, the gadolinium oxide may comprise between about 3.15 mol % and about 4.50 mol % based on the total molar amounts of zirconium dioxide, cerium oxide, gadolinium oxide, tantalum pentoxide, and niobium pentoxide in the at least a portion of the ceramic biomedical implant.

The fired ceramic piece may comprise a combined concentration of zirconium dioxide, cerium oxide, yttrium oxide, gadolinium oxide, tantalum pentoxide, and niobium pentoxide in an amount of no more than about 25% of the fired ceramic piece by volume. In some such embodiments and implementations, the fired ceramic piece may comprise a combined concentration of zirconium dioxide, cerium oxide, yttrium oxide, gadolinium oxide, tantalum pentoxide, and niobium pentoxide in an amount of no more than about 16% of the fired ceramic piece by volume.

The fired ceramic piece may further comprise aluminum oxide, yttrium oxide, strontium oxide, magnesium oxide, titanium dioxide, and calcium oxide. In some embodiments and implementations, the fired ceramic piece may further comprise cerium oxide.

The fired ceramic piece may comprise a biomedical implant. In some such embodiments and implementations, the biomedical implant may be manufactured so as to have a three-point flexural strength of at least about 1,000 MPa, and/or a fracture toughness of at least about 6.5 MPa·m$^{1/2}$.

In another example of an implementation of a method for manufacturing a ceramic biomedical implant, the method may comprise preparing a slurry comprising ingredients configured to yield a ceramic piece comprising at least aluminum oxide, zirconium dioxide, strontium oxide, magnesium oxide, titanium dioxide, and calcium oxide. A trivalent dopant may be added to the slurry. The trivalent dopant may comprise yttrium oxide and/or gadolinium oxide, and wherein the trivalent dopant comprises a concentration of between about 1.5 mol % and about 6.5 mol % based on the total molar amounts of zirconium dioxide, cerium oxide, yttrium oxide, gadolinium oxide, tantalum pentoxide, and niobium pentoxide in the slurry.

A pentavalent dopant may be added to the slurry. The pentavalent dopant may comprise a combination of tantalum pentoxide and/or niobium pentoxide. The pentavalent dopant may comprise a concentration of between about 1.5 mol % and about 6.5 mol % based on the total molar amounts of zirconium dioxide, cerium oxide, yttrium oxide, gadolinium oxide, tantalum pentoxide, and niobium pentoxide in the slurry. In some embodiments and implementations, the molar concentration of the trivalent dopant may be at least substantially identical to the molar concentration of the pentavalent dopant.

The slurry may be dried such as, for example, by way of a spray drying process, and/or compressed, to form a compact. The compact may then be fired to obtain a fired ceramic piece comprising at least aluminum oxide, zirconium dioxide, yttrium oxide, strontium oxide, magnesium oxide, titanium dioxide, and calcium oxide. The fired ceramic piece may comprise aluminum oxide in a concentration of at least about 74% by weight, and may further comprise zirconium dioxide in a concentration of between about 21% and about 24% by weight.

The fired ceramic piece may further comprise strontium oxide in a concentration of about between about 0.8% and about 1.2% by weight, and a combined concentration of magnesium oxide, titanium dioxide, and calcium oxide in a concentration of about 0.3% by weight. In some embodiments and implementations, these concentrations may be less than or equal to about 0.05% of the entire composition by weight (in some embodiments, equal to about 0.05% of the entire composition by weight), less than or equal to about 0.10% of the entire composition by weight (in some embodiments, equal to about 0.10% of the entire composition by weight), and about 0.15% of the entire composition by weight, respectively.

In some embodiments and implementations, cerium oxide may be added to the slurry. In some such embodiments and implementations, the cerium oxide may be added to the slurry in a concentration of no more than about 3.0 mol % based on the total molar amounts of zirconium dioxide, cerium oxide, yttrium oxide, gadolinium oxide, tantalum pentoxide, and niobium pentoxide in the slurry.

Various embodiments of the invention are contemplated in which any one or more of the embodiments of the invention are contemplated in which ceramic pieces and/or biomedical implants comprise one or more such concentrations and/or concentration ranges disclosed herein.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
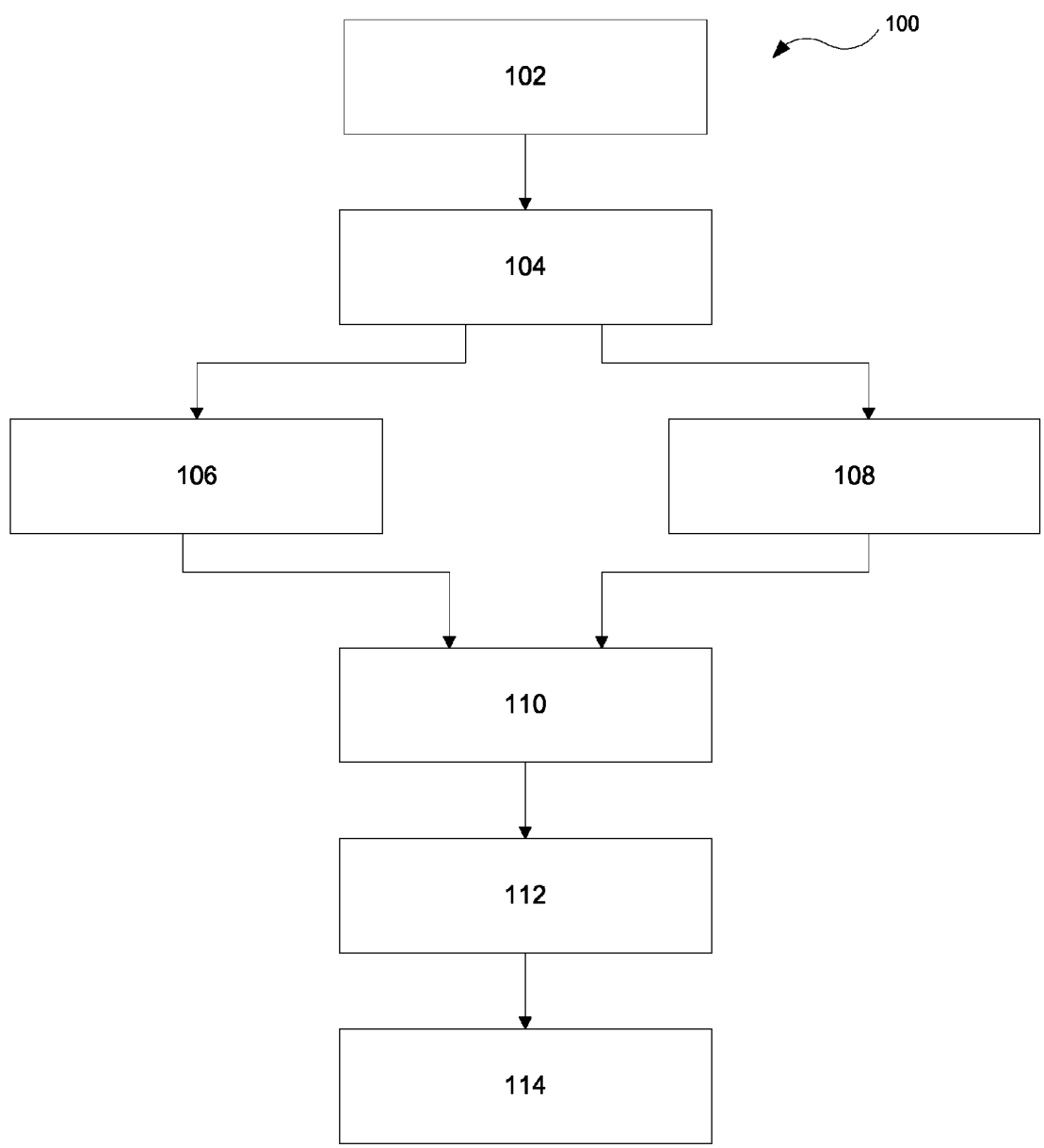
FIG. 1 is a flow chart illustrating one example of a method for manufacturing a doped alumina-zirconia ceramic material suitable for use as a biomedical implant.

It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail.

Various embodiments of apparatus, materials, methods, and systems are disclosed herein that relate to biomedical implants and other devices made up of unique alumina-zirconia ceramic materials having specific dopants. In some embodiments, these materials may be used to form various structural members, such as human endoprostheses and other biomedical implants. Examples of such implantable devices that may benefit from one or more of the unique materials and/or methods disclosed herein include, but are not limited to, artificial hips, knees, shoulders, ankles and phalange joints, spinal articulation devices and other spinal implants, and dental implants, such as abutments, crowns, and bridges. The compositions and processing methods provided in this disclosure may provide devices that have high fracture strength and toughness, and have improved resistance to low-temperature degradation (LTD).

Alumina has become one of the most widely used ceramic materials for total hip arthroplasty. An industrial specification was developed for its composition, processing and properties, and it has been shown to be biocompatible and to possess high hardness and a low coefficient of friction. These characteristics reduce the occurrence of wear debris. However, alumina also has a relatively low fracture strength and toughness, both of which increase the risk of catastrophic in-vivo failure.

To overcome this problem, zirconia was investigated and added as an alternative ceramic, either in its partially stabilized form using magnesia, or with yttria to form Tetragonal Zirconia Polycrystals (TZP). These compositions greatly improved upon the strength and toughness of alumina and, moreover, they had lower coefficients of friction and wear. These materials derived much of their improved characteristics by taking advantage of a polymorphic phase transformation that occurs in doped-zirconia known as transformation-toughening. This transformation involves the meta-stabilization of the high-temperature tetragonal phase through the incorporation of magnesia, yttria, or other dopants.

In the presence of an advancing crack, the metastable tetragonal phase transforms to its stable monoclinic form, typically with an accompanying volume increase of about 5%. This sudden volume change exerts compressive forces on the crack tip, thereby slowing or arresting its propagation. Partially stabilized zirconia ("PSZ") implants are still available, and an industrial standard for their composition, processing, and properties has been created. However, after more than a decade of use, TZP implants were withdrawn from the marketplace in 2001, and the industrial standard supporting their use has since been abandoned. The abandonment of TZP is attributable primarily to one severe weakness—it spontaneously transforms to its stable monoclinic form under in-vivo hydrothermal conditions. This effect has become known as low-temperature degradation (LTD). This transformation results in increased implant surface roughness, enhanced wear, weakening of the material, and often eventual fracture.

Zirconia-Toughened Alumina (ZTA) and Alumina Matrix Composites (AMC) were then introduced to the marketplace in an attempt to overcome TZP's limitations. ZTA is a fully dense composite ceramic consisting typically of TZP in an alumina matrix. AMC is a special ZTA composition consisting of $ZrO_2$ and mixed oxides consisting of $Y_2O_3$, $Cr_2O_3$, and SrO, along with alumina.

ZTA/AMC materials are bio-inert, and typically have good strength, toughness, and hardness properties. These materials are also often highly abrasion- and wear-resistant. For total hip arthroplasty ("THA devices"), ZTA/AMC components typically provide equivalent or lower wear rates than alumina or TZP. However, ZTA and AMC also achieve their mechanical property improvements through transformation toughening, and concerns remain about their in-vivo hydrothermal stability.

As such, in order to overcome one or more of the limitations of the prior art, as discussed above or otherwise, various embodiments disclosed herein may provide for an alumina zirconia composite composition and/or related processing methods that may be used to form ceramic implants with high fracture strength, high toughness, and improved resistance to low-temperature hydrothermal degradation. In some embodiments, these benefits may be obtained at least in part by adding dopants to the composition, such as charge compensating dopants.

Without being limited by theory, it has been proposed that the presence of excess oxygen vacancies in a zirconia lattice may enable an LTD process to proceed at an increased pace. As such, eliminating excess oxygen vacancies may be used to slow or stop LTD.

In some embodiments, the charge-compensating dopants may comprise, for example, $Y^{3+}$ paired with $Nb^{5+}$ or $Ta^{5+}$. Some embodiments may comprise equal, or at least approximately equal, amounts of +3 and +5 valence cations, which may contribute to minimization of oxygen vacancies in the zirconia lattice and/or resistance of LTD behavior.

In some embodiments, the $Al_2O_3$ concentration in the composition is greater than about 75% of the entire composition by weight. In some embodiments, the $Al_2O_3$ concentration in the composition is greater than about 74% of the entire composition by weight. In some such embodiments, the $Al_2O_3$ concentration in the composition is greater than about 74.6% of the entire composition by weight. It is anticipated, however, that the desired percentage of alumina may vary in accordance with the variance of other ingredients that may also be included in the composition, such as SrO, MgO, $TiO_2$, CaO, $ZrO_2$, $Y_2O_3$, $Gd_2O_3$, $Ta_2O_5$, $Nb_2O_5$, and $CeO_2$.

In some embodiments, the combination of $Al_2O_3$, SrO, MgO, $TiO_2$, and CaO is greater than about 84% of the entire composition by volume. Keeping these constituents above this volumetric concentration appears to substantially eliminate, or at least minimize, water percolation into the ceramic body, and thereby minimizes LTD. However, as discussed below, this combination percentage may be decreased for certain embodiments, particularly when charge-compensating dopants are used.

In some embodiments, the $ZrO_2$ content may be within a range of between about 21% of the entire composition by weight and about 24% of the entire composition by weight. In some embodiments, stabilization additives may be added to the composition. For example, $Y_2O_3$, $Gd_2O_3$, $Ta_2O_5$, $Nb_2O_5$, and/or $CeO_2$ may be added as stabilization additives. In some such embodiments, the combination of $ZrO_2$ and stabilization additives may be less than or equal to about 16% of the entire composition by volume. Thus, for example, in some such embodiments, the combination of the $ZrO_2$ along with $Y_2O_3$, $Gd_2O_3$, $Ta_2O_5$, $Nb_2O_5$, and/or $CeO_2$ may be less than or equal to about 16% of the entire composition by volume. These particular compositions appear to substantially eliminate, or at least minimize, LTD through percolation.

However, it is contemplated that, in other embodiments, the addition of charge-compensating dopants may provide for sufficient protection that the zirconia concentration may be increased while still substantially reducing LTD. For example, in some embodiments, the combination of $ZrO_2$ and stabilization additives may be up to about 25% of the entire composition by volume.

As mentioned above, some embodiments may comprise one or more dopants to further decrease LTD and/or otherwise improve desirable characteristics of the implant or device. In some embodiments, such dopants may comprise trivalent dopants, such as Yttria ($Y_2O_3$) and/or Gadolinia ($Gd_2O_3$) and pentavalent dopants, such as Tantala ($Ta_2O_5$) and/or Niobia ($Nb_2O_5$), as discussed below. In some embodiments, the trivalent dopant content may be within a range of about 1.5 mol % to 6.5 mol % based on the total molar amounts of, for example, $ZrO_2$, $CeO_2$, $Y_2O_3$, $Gd_2O_3$, $Ta_2O_5$, and $Nb_2O_5$. In some such embodiments and implementations, the trivalent dopant content may be within a range of about 3.0 mol % and about 5.0 mol % based on the total molar amounts of zirconium dioxide, cerium oxide, yttrium oxide, gadolinium oxide, tantalum pentoxide, and/or niobium pentoxide in the composition.

It is thought that concentrations of trivalent dopants below the range referenced above may not provide sufficient stabilization, whereas higher concentrations may lead to non-transformable compositions that exhibit significantly lower strength and fracture toughness. $Y_2O_3$ and $Gd_2O_3$ may be interchangeable with one another in the batch for certain embodiments and implementations.

In some embodiments, the pentavalent dopant content may also be within a range of about 1.5 mol % to 6.5 mol % based on the total molar amounts of, for example, $ZrO_2$, $CeO_2$, $Y_2O_3$, $Gd_2O_3$, $Ta_2O_5$, and $Nb_2O_5$. In some such embodiments, the pentavalent dopant content may also be within a range of about 3.0 mol % and about 5.0 mol % based on the total molar amounts of zirconium dioxide, cerium oxide, yttrium oxide, gadolinium oxide, tantalum pentoxide, and/or niobium pentoxide in the composition.

It is thought that concentrations of pentavalent dopant below the range referenced above may not provide sufficient stabilization, whereas higher concentrations may lead to non-transformable compositions that exhibit significantly lower strength and fracture toughness. $Nb_2O_5$ and $Ta_2O_5$ may be interchangeable with one another in the batch for certain embodiments and implementations. In some embodiments, the total mol % of pentavalent dopant is equal, or at least substantially equal, to the total mol % of trivalent dopant in order to minimize LTD susceptibility.

In some embodiments and implementations, the one or more trivalent dopants may comprise any cation with a stable oxidation state of +3 and having an ionic radius between that of lutetium 3+ and that of praseodymium 3+. Thus, for example, in some embodiments and implementations, neodymium, yttrium, and/or gadolinium may be used as a trivalent dopant.

Similarly, in some embodiments and implementations, the one or more pentavalent dopants may comprise any cation with a stable oxidation state of +5 and an ionic radius between that of vanadium and niobium/tantalum. Thus, for example, in some embodiments and implementations, tantalum, niobium, and/or vanadium may be used as a pentavalent dopant.

In some embodiments, the concentration of ceria ($CeO_2$) may be within a range of between about 0% and about 3.0% by mole based on the total molar amounts in the composition. For example, in embodiments containing $ZrO_2$, $CeO_2$, $Y_2O_3$, $Gd_2O_3$, $Ta_2O_5$, and $Nb_2O_5$, the $CeO_2$ content may be within a range of between about 0% and about 3.0% by mole based on the total molar amounts of $ZrO_2$, $CeO_2$, $Y_2O_3$, $Gd_2O_3$, $Ta_2O_5$, and $Nb_2O_5$. In some embodiments, $CeO_2$ may be added to the composition in lieu of at least a portion of the charge-compensating dopants. However, it is expected that use of Ceria exclusively rather than charge-compensating dopants may be insufficient to adequately stabilize the tetragonal phase of the zirconia. Higher concentrations than those listed above may result in cracking of the ceramic body during re-oxidation heat treatments subsequent to hot isostatic pressing in a reducing environment.

In some embodiments, the concentration of strontia (SrO) may be between about 0.8% and about 1.2% of the entire composition by weight. In some such embodiments, the concentration of SrO may be equal to about 0.8% of the entire composition by weight. In some implementations of desired methods in accordance with the present disclosure, SrO may be added to the composition as strontium aluminate ($SrAl_2O_4$). The addition of this ingredient may be desirable for certain applications to provide platelet type grains, which may provide additional strength and toughness to the ceramic body.

In some embodiments, the concentration of magnesia (MgO) may be less than or equal to about 0.05% of the entire composition by weight. In some such embodiments, the concentration of MgO may be equal to about 0.05% of the entire composition by weight. MgO may be added to the composition as a sintering aid and may also serve as an alumina grain growth inhibitor. In some implementations of desired methods in accordance with the present disclosure, MgO may be added to the composition as magnesium aluminate ($MgAl_2O_4$).

In some embodiments, the concentration of titania ($TiO_2$) may be less than or equal to about 0.10% of the entire composition by weight. In some such embodiments, the concentration of $TiO_2$ may be equal to about 0.10% of the entire composition by weight. $TiO_2$ may also be added to the composition as a sintering aid.

In some embodiments, the concentration of calcia (CaO) may be about 0.15% of the entire composition by weight. CaO may also be added to the composition as a sintering aid. In some implementations of desired methods in accordance with the present disclosure, CaO may be added to the composition as calcium aluminate ($CaAl_2O_4$).

In embodiments containing MgO in combination with $TiO_2$ and CaO, these ingredients may form a low melting eutectic that may serve to lower the sintering temperature and may further allow for the production of a ceramic body with a finer grain size, higher fracture strength, and toughness. For certain applications, it may be desirable to keep the total concentration of the combination of the sintering aids at less than or equal to about 0.3% of the entire composition by weight. For example, in some embodiments, the total combined concentration of MgO, $TiO_2$, and CaO may be less than or equal to about 0.3% of the entire composition by weight.

In some embodiments, the combination of sintering aids may be equal to about 0.3% of the entire composition by weight. In some such embodiments, the combination of MgO, $TiO_2$, and CaO may be approximately equal to about 0.3% of the entire composition by weight. In other embodiments, the combination of sintering aids may be less than 0.3% of the entire composition by weight. For example, the combination of MgO, $TiO_2$, and CaO may be less than 0.3% of the entire composition by weight.

For some implementations, concentrations of these ingredients (or the combination of other sintering aids) higher than about 0.3% of the entire composition by weight may lead to the development of a glassy grain-boundary phase in the dense ceramic, which may potentially result in lower strength and toughness, whereas concentrations significantly lower than about 0.3% of the entire composition by weight may be insufficient to provide for adequate densification.

In one specific example of a composition according to one or more of the principles disclosed herein, the composition may comprise about 18.95% by weight of $ZrO_2$ about 2.42% by weight of $Gd_2O_3$, about 2.95% by weight of $Ta_2O_5$, about 1.60% by weight of $SrAl_2O_4$, about 0.42% by weight of $CaAl_2O_4$, about 0.18% by weight of $MgAl_2O_4$, about 0.10% by weight of $TiO_2$, and about 73.38% by weight of $Al_2O_3$. This specific composition may comprise about 92 mol % of $ZrO_2$, about 4 mol % of $Gd_2O_3$, and about 4 mol % of $Ta_2O_5$ within the phase comprising $ZrO_2$, $Gd_2O_3$, and $Ta_2O_5$ in the composition. It should be understood, however, that these percentages and/or ingredients may vary in other implementations and embodiments, as suggested elsewhere in this disclosure.

A particular exemplary method 100 for creating a ceramic implant is illustrated in FIG. 1. In this method, one or more feedstocks may be prepared for the $SrAl_2O_4$ and $CaAl_2O_4$ at 102 by mixing $SrCO_3$ or $CaCO_3$ with $Al_2O_3$, respectively.

In some implementations of methods for creating a ceramic material, such as a ceramic implant, having these or other ingredients, commercially available ceramic powders may be used, such as Tosoh™ TZ-0 or TZ-3Y (Tokyo, Japan) or Inframat™ Advanced Materials (Manchester, Conn.) 0 and 3 mol % $ZrO_2$. Additionally, or alternatively, Inframat™ $CeO_2$, Spectrum Chemical™ (Los Angeles, Calif.), $CaCO_3$, $SrCO_3$ and $TiO_2$, Sasol Ceralox™ (Tuscon, Ariz.) AHPA-0.5 $Al_2O_3$, and/or AHPA Spinel™ AF ($MgAl_2O_4$) may be used.

The feedstock(s) may be prepared for, for example the $SrAl_2O_4$ and $CaAl_2O_4$, by mixing $SrCO_3$ or $CaCO_3$ with $Al_2O_3$, respectively. This may be done using, for example, vibratory, ball, or attrition milling in water with appropriate dispersants for about 8 to about 24 hours. Many such dispersants may be used, as those of ordinary skill in the art will appreciate. For example, a combination of ammonium hydroxide and citric acid may be used for certain implementations, which may be desirable for performing a suitable pH adjustment. The step 102 of preparing the feedstock(s) may further comprise centrifuging the mixed constituents to remove excess water, after which the resulting cakes may be dried in an oven. A dry-ball mill deagglomeration step may then be conducted to break down soft agglomerates.

The feedstock(s) may then be calcined at step 104. In some implementations, step 104 may comprise calcining the feedstock(s) in air at between about 1100° C. and about 1300° C. for approximately 2 hours.

The feedstock(s) may then be weighed and added to the batch in their appropriate proportions, along with the remaining constituents, as indicated at the green state forming step depicted at 106, to create a slurry. Step 106 may further comprise subjecting the feedstock(s), in combination with the remaining raw materials (together, the slurry), to vibratory, ball, or attrition milling for about 8 to about 24 hours in water, along with appropriate dispersants. A binder may also be added to the batch at the end of the mixing/milling operations, after which the slurry containing the constituents may be dried. Various binders may be used, as those of ordinary skill in the art will appreciate. For example, in some implementations, an acrylic copolymer known under the name Rhoplex B-60A™ may be used. The drying may take place, for example, in a conventional countercurrent, two fluid nozzle atomization spray dryer. The material may then be sieved. An external lubricant may also be added, if desired, such as Acrawax C™.

In some implementations, a green state forming method/step(s) may comprise mixing, dispersing, and/or milling feedstocks and raw powders, as referenced above, after which an alternative green forming step 108 may be employed in place of step 106. In some implementations, step 108 may comprise a Lange's Colloidal Isopressing process, wherein the dispersed, milled slurry is infused with a salt to create a weakly attractive particle network. This slurry may then be consolidated via, for example, pressure filtration. In some implementations, the pressure filtration may be below the ductile-to-brittle transition pressure to achieve a plastic, high solids loading slurry. Further details for determining such pressures may be found in U.S. Pat. No. 6,787,080 titled "Colloidal Isopressing," the entire contents of which are hereby incorporated by reference herein.

Finally, step 108 may further comprise isostatically pressing the consolidated slurry/compact in a mold cast into a desired shape. In some implementations, this may be done at pressures between about 150 MPa and about 300 MPa. In some implementations, step 108 may, like step 106, comprise use of a binder. However, it is thought that use of a lubricant would be unnecessary in methods comprising step 108 rather than step 106.

As indicated at step 110, components from one or both of the green state forming steps (106 and 108) may then be fired in, for example, an electric air atmosphere kiln. This may be done, in some implementations, at temperatures between about 1450° C. and about 1600° C. for up to 2 hours.

These components may then be hot isostatically pressed at step 112. In some implementations, this may be done at temperatures between about 1400° C. and about 1500° C. in nitrogen or argon gas at pressures of between about 130 MPa and about 210 MPa. In some implementations, the hot isostatic pressing may be done for about 1 to 2 hours.

The components may then be re-oxidized at step 114. Step 114 may be performed using an electric air atmosphere kiln at temperatures between about 1250° C. and about 1400° C. for time periods ranging from about 2 to 48 hours.

It has been discovered that many embodiments of components, such as biomedical implants, produced and processed according to one or more principles, implementations, and/or embodiments of this disclosure have 3-point flexural strengths of at least about 1,000 MPa and fracture toughnesses of at least about 6.5 MPa·m$^{1/2}$. Such embodiments may also exhibit minimal low temperature hydrothermal degradation after being exposed to saturated steam autoclave environments of 120° to 134° C. for up to 100 hours.

EXAMPLE 1

Figure 2:
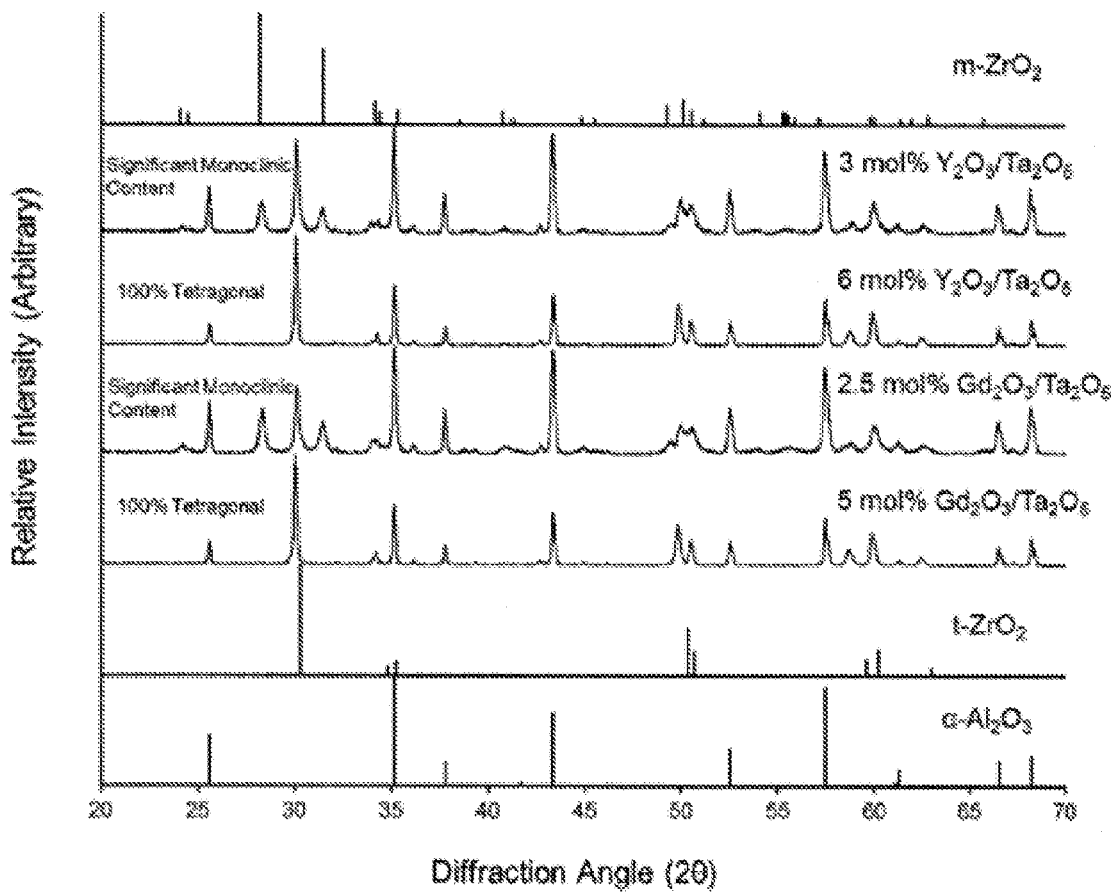
FIG. 2 is a graph illustrating the results of a study involving concentrations of charge-compensating dopants with various embodiments of alumina-zirconia ceramic components.

In a first working example, several embodiments of ceramic components were manufactured using the principles disclosed herein. The results of a study of these components are depicted in the graph of FIG. 2. As shown in FIG. 2, this study comprised use of ceramic components comprising various concentrations of charge-compensating dopants used in ZTA materials. The chart of FIG. 2 plots x-ray diffraction spectra as relative intensity as a function of the diffraction angle for each sample material.

The components used in the study comprise $Gd_2O_3/Ta_2O_5$ and $Y_2O_3/Ta_2O_5$ ceramic compositions having dopant concentrations of 2.5 and 5% by mole for the $Gd_2O_3/Ta_2O_5$ composition and 3 and 6% by mole for $Y_2O_3/Ta_2O_5$ composition. The study was focused upon establishing the bounds of dopant concentration for charge-compensating schemes in ZTA materials. Standard data for monoclinic $ZrO_2$, tetragonal $ZrO_2$, and $\alpha$-$Al_2O_3$ are also plotted in FIG. 2 for reference.

As can be seen in FIG. 2, components produced and processed according to this disclosure exhibit mixed monoclinic and tetragonal zirconia content at the low end of the dopant mole fraction spectrum and 100% tetragonal zirconia content at the high end of the dopant mole fraction spectrum. Therefore, it is believed that the range of dopant compositions described in this disclosure may at least roughly represent the boundaries of the transformable region of the phase diagram. The material should be transformable in order for the composite to exhibit desired strength and fracture toughness.

These results suggest that embodiments having a trivalent dopant content within a range of about 1.5 mol % to 5.5 mol % based on the total molar amounts of, for example, $ZrO_2$, $CeO_2$, $Y_2O_3$, $Gd_2O_3$, $Ta_2O_5$, and/or $Nb_2O_5$, may be preferred for certain uses. $Y_2O_3$ and $Gd_2O_3$ may be at least relatively interchangeable with one another in the batch for certain embodiments and implementations. Thus, the amounts of $Y_2O_3$ disclosed herein may generally be substituted for $Gd_2O_3$, and vice versa. Similarly, any such amounts may generally comprise any suitable combination of $Gd_2O_3$ and $Y_2O_3$.

As with the trivalent dopants, the pentavalent dopant content may be within a range of about 1.5 mol % to 5.5 mol % based on the total molar amounts of, for example, $ZrO_2$, $CeO_2$, $Y_2O_3$, $Gd_2O_3$, $Ta_2O_5$, and/or $Nb_2O_5$. $Ta_2O_5$ and $Nb_2O_5$ may be interchangeable such that the combination of the two is at least approximately equal to the proposed concentration of one of the two.

However, the test results further suggest that slightly less $Gd_2O_5$ may be needed in order to achieve the same effect as a given amount of $Y_2O_3$. Thus, in some preferred embodiments, the trivalent and pentavalent dopant contents may both be within a range of about 3.25 mol % to about 4.75 mol % for compositions comprising $Y_2O_3$ with $Nb_2O_5$ or $Ta_2O_5$ and may both be within a range of about 3.15 mol % to about 4.50 mol % for compositions comprising $Gd_2O_3$ with $Nb_2O_5$ or $Ta_2O_5$.

It is also contemplated that some of the ranges presented above may be shifted or expanded under certain conditions. For example, under the condition that the ratio of zirconia (plus dopants) to alumina is increased, the useful range of the dopant ranges may be expanded. For example, in embodiments in which this ratio is no more than about 25/75 by volume, the trivalent/pentavalent ranges may both be between about 2.0 mol % to about 7.0 mol %. This relationship between the ratio of zirconia to alumina and the width of the preferred ranges of the trivalent and pentavalent dopants may be related on a sliding scale such that, as the aforementioned ratio is decreased, the most useful trivalent and pentavalent dopant ranges tighten.

$Nb_2O_5$ and $Ta_2O_5$ may be interchangeable with one another in the batch for certain embodiments and implementations such that any mention of $Nb_2O_5$ herein may instead refer to $Ta_2O_5$, and vice versa. Similarly, the amounts of $Nb_2O_5$ disclosed herein may generally be substituted for $Ta_2O_5$, and vice versa. Further, any such amounts may generally comprise any suitable combination of $Nb_2O_5$ and $Ta_2O_5$ rather than just one of these compounds.

In view of the foregoing, it should be appreciated that, certain preferred embodiments and implementations may be characterized in that the molar concentration of $Y_2O_3$ and/or $Gd_2O_3$ is at least approximately equal to the molar concentration of $Nb_2O_5$ and/or $Ta_2O_5$ and the molar amounts fall within the ranges presented herein. In some embodiments, the molar amounts presented herein for $Ta_2O_5$ may be substituted for $Nb_2O_5$, and vice versa and, similarly, the molar amounts presented herein for $Y_2O_3$ may be substituted $Gd_2O_3$. To state this principle otherwise, any mention of a molar concentration of either $Y_2O_3$ and $Gd_2O_3$ may be replaced with any combination of $Y_2O_3$ and $Gd_2O_3$ that together add to such concentration and, likewise, any mention of a molar concentration of either $Nb_2O_5$ or $Ta_2O_5$ may be replaced with a combination of a molar concentration of $Nb_2O_5$ and $Ta_2O_5$ that together add to such concentration.

Moreover, it should be understood that, although an at least substantially identical molar concentration of $Y_2O_3$ and/or $Gd_2O_3$ relative to $Nb_2O_5$ and/or $Ta_2O_5$ is preferred, significant improvement may be achieved by compositions in which these two concentrations are within at least about 0.5 mol % of one another.

Ceramic components formed in accordance with one or more principles, implementations, or embodiments of this disclosure can be shaped and machined into useful human endoprostheses, including but not limited to artificial hips, knees, shoulders, ankles and phalange joints, and/or articulation devices in the spine, as well as dental implants, abutments, crowns and bridges.

It will be understood by those having skill in the art that changes may be made to the details of the above-described embodiments without departing from the underlying principles presented herein. For example, any suitable combination of various embodiments, or the features thereof, is contemplated.

In any methods disclosed herein comprising one or more steps or actions for performing the described method, the method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein. The scope of the present invention should, therefore, be determined only by the following claims.

The invention claimed is:

1. A method for manufacturing a ceramic biomedical implant, the method comprising the steps of:
   preparing a first feedstock;
   preparing a second feedstock;
   preparing a slurry comprising materials from the first feedstock, materials from the second feedstock, and further comprising:
     one or more trivalent dopants comprising at least one of yttrium oxide and gadolinium oxide;
     one or more pentavalent dopants comprising at least one of tantalum pentoxide and niobium pentoxide, wherein the one or more trivalent dopants are within no more than about 0.5 mol % of the one or more pentavalent dopants; and one or more additional ingredients comprising or configured to yield at least a portion of a ceramic biomedical implant comprising at least zirconium dioxide, aluminum oxide, at least one of yttrium oxide and gadolinium oxide, and at least one of tantalum pentoxide and niobium pentoxide, wherein the one or more trivalent dopants comprise between about 1.5 mol % and about 6.5 mol % based on the total molar amounts of zirconium dioxide, cerium oxide, yttrium oxide, gadolinium oxide, tantalum pentoxide, and niobium pentoxide in the at least a portion of the ceramic biomedical implant, wherein the at least a portion of the ceramic biomedical implant further comprises at least strontium oxide, magnesium oxide, titanium dioxide, and calcium oxide, wherein the at least a portion of the ceramic biomedical implant comprises a combination of aluminum oxide, strontium oxide, magnesium oxide, titanium dioxide, and calcium oxide in a concentration of at least about 84% by volume, and wherein the one or more pentavalent dopants comprise between about 1.5 mol % and about 6.5 mol % based on the total molar amounts of zirconium dioxide, cerium oxide, yttrium oxide, gadolinium oxide, tantalum pentoxide, and niobium pentoxide in the at least a portion of the ceramic biomedical implant.

2. The method of claim 1, wherein the one or more additional ingredients further comprises cerium oxide.

3. The method of claim 2, wherein the cerium oxide comprises no more than about 3.0% by mole based on the total molar amounts in the at least a portion of the ceramic biomedical implant.

4. The method of claim 1, wherein the molar concentration of the one or more trivalent dopants is at least substantially identical to the molar concentration of the one or more pentavalent dopants.

5. The method of claim 1, wherein the at least a portion of the ceramic biomedical implant comprises aluminum oxide in a concentration of at least about 74% by weight.

6. The method of claim 5, wherein the at least a portion of the ceramic biomedical implant comprises aluminum oxide in a concentration of at least about 74.6% by weight.

7. The method of claim 1, wherein the step of preparing the first feedstock comprises mixing ingredients comprising at least aluminum oxide and strontium carbonate or ingredients selected to yield aluminum oxide and strontium carbonate, and wherein the step of preparing the second feedstock comprises mixing ingredients comprising at least aluminum oxide and calcium carbonate or ingredients selected to yield aluminum oxide and calcium carbonate.

8. A method for manufacturing a ceramic piece, the method comprising the steps of:
preparing a slurry comprising, or comprising ingredients configured to yield a ceramic piece comprising, at least:
aluminum oxide;
zirconium dioxide;
a trivalent dopant comprising yttrium oxide; and
one or more pentavalent dopants comprising at least one of tantalum pentoxide and niobium pentoxide, wherein the trivalent dopant is within no more than about 0.5 mol % of the one or more pentavalent dopants, wherein the yttrium oxide comprises between about 3.25 mol % and about 4.75 mol % based on the total molar amounts of zirconium dioxide, cerium oxide, yttrium oxide, tantalum pentoxide, and niobium pentoxide in the at least a portion of the ceramic biomedical implant, and wherein the one or more pentavalent dopants comprise between about 1.5 mol % and about 6.5 mol % based on the total molar amounts of zirconium dioxide, cerium oxide, yttrium oxide, tantalum pentoxide, and niobium pentoxide in the at least a portion of the ceramic biomedical implant; and
firing a compact derived from the slurry to obtain a fired ceramic piece comprising zirconium dioxide in a concentration of between about 21% and about 24% by weight of the fired ceramic piece.

9. The method of claim 8, wherein the fired ceramic piece comprises a combined concentration of zirconium dioxide, cerium oxide, yttrium oxide, tantalum pentoxide, and niobium pentoxide in an amount of no more than about 25% of the fired ceramic piece by volume.

10. The method of claim 9, wherein the fired ceramic piece comprises a combined concentration of zirconium dioxide, cerium oxide, yttrium oxide, tantalum pentoxide, and niobium pentoxide in an amount of no more than about 16% of the fired ceramic piece by volume.

11. The method of claim 8, wherein the fired ceramic piece further comprises aluminum oxide, yttrium oxide, strontium oxide, magnesium oxide, titanium dioxide, and calcium oxide.

12. The method of claim 11, wherein the fired ceramic piece further comprises cerium oxide.

13. The method of claim 8, wherein the molar concentration of the trivalent dopant is at least substantially identical to the molar concentration of the one or more pentavalent dopants.

14. The method of claim 8, wherein the fired ceramic piece comprises a biomedical implant, wherein the biomedical implant comprises a three-point flexural strength of at least about 1,000 MPa, and wherein the biomedical implant further comprises a fracture toughness of at least about $6.5 \text{ MPa} \cdot \text{m}^{1/2}$.

15. A method for manufacturing a ceramic biomedical implant, the method comprising the steps of:
preparing a slurry comprising ingredients configured to yield a ceramic piece comprising at least aluminum oxide, zirconium dioxide, strontium oxide, magnesium oxide, titanium dioxide, and calcium oxide;
adding a trivalent dopant to the slurry, wherein the trivalent dopant comprises yttrium oxide and/or gadolinium oxide, and wherein the trivalent dopant comprises a concentration of between about 1.5 mol % and about 6.5 mol % based on the total molar amounts of zirconium dioxide, cerium oxide, yttrium oxide, gadolinium oxide, tantalum pentoxide, and niobium pentoxide in the slurry;
adding a pentavalent dopant to the slurry, wherein the pentavalent dopant comprises tantalum pentoxide and/or niobium pentoxide, wherein the pentavalent dopant comprises a concentration of between about 1.5 mol % and about 6.5 mol % based on the total molar amounts of zirconium dioxide, cerium oxide, yttrium oxide, gadolinium oxide, tantalum pentoxide, and niobium pentoxide in the slurry, and wherein the molar concentration of the trivalent dopant is at least substantially identical to the molar concentration of the pentavalent dopant;
firing a compact derived from the slurry to obtain a fired ceramic piece comprising at least aluminum oxide, zirconium dioxide, yttrium oxide, strontium oxide, magnesium oxide, titanium dioxide, and calcium oxide,
wherein the fired ceramic piece comprises aluminum oxide in a concentration of at least about 74% by weight, wherein the fired ceramic piece comprises zirconium dioxide in a concentration of between about 21% and about 24% by weight,
wherein the fired ceramic piece comprises strontium oxide in a concentration of about between about 0.8% and about 1.2% by weight,
wherein the fired ceramic piece comprises a combined concentration of magnesium oxide, titanium dioxide, and calcium oxide in a concentration of about 0.3% by weight, and
wherein the fired ceramic piece comprises a combination of aluminum oxide, strontium oxide, magnesium oxide, titanium dioxide, and calcium oxide in a concentration of at least about 84% by volume.

16. The method of claim 15, further comprising adding cerium oxide to the slurry.

17. The method of claim 16, wherein the cerium oxide is added to the slurry in a concentration of no more than about 3.0 mol % based on the total molar amounts of zirconium dioxide, cerium oxide, yttrium oxide, gadolinium oxide, tantalum pentoxide, and niobium pentoxide in the slurry.

18. A method for manufacturing a ceramic piece, the method comprising the steps of:
preparing a slurry comprising, or comprising ingredients configured to yield a ceramic piece comprising, at least:
aluminum oxide;
zirconium dioxide;
one or more trivalent dopants comprising at least one of yttrium oxide and gadolinium oxide; and
one or more pentavalent dopants comprising at least one of tantalum pentoxide and niobium pentoxide, wherein the one or more trivalent dopants are within no more than about 0.5 mol % of the one or more pentavalent dopants; and
firing a compact derived from the slurry to obtain a fired ceramic piece comprising zirconium dioxide in a concentration of between about 21% and about 24% by weight of the fired ceramic piece, wherein the fired ceramic piece comprises a combined concentration of zirconium dioxide, cerium oxide, yttrium oxide, gadolinium oxide, tantalum pentoxide, and niobium pentoxide in an amount of no more than about 25% of the fired ceramic piece by volume.

19. The method of claim 18, wherein the fired ceramic piece comprises a combined concentration of zirconium dioxide, cerium oxide, yttrium oxide, gadolinium oxide, tantalum pentoxide, and niobium pentoxide in an amount of no more than about 16% of the fired ceramic piece by volume.

20. A method for manufacturing a ceramic piece, the method comprising the steps of:
preparing a slurry comprising, or comprising ingredients configured to yield a ceramic piece comprising, at least:
aluminum oxide;
zirconium dioxide;
a trivalent dopant comprising gadolinium oxide; and
one or more pentavalent dopants comprising at least one of tantalum pentoxide and niobium pentoxide, wherein the trivalent dopant is within no more than about 0.5 mol % of the one or more pentavalent dopants, wherein the gadolinium oxide comprises between about 3.15 mol % and about 4.50 mol % based on the total molar amounts of zirconium dioxide, cerium oxide, gadolinium oxide, tantalum pentoxide, and niobium pentoxide in the at least a portion of the ceramic biomedical implant, and wherein the one or more pentavalent dopants comprise between about 1.5 mol % and about 6.5 mol % based on the total molar amounts of zirconium dioxide, cerium oxide, tantalum pentoxide, and niobium pentoxide in the at least a portion of the ceramic biomedical implant; and
firing a compact derived from the slurry to obtain a fired ceramic piece comprising zirconium dioxide in a concentration of between about 21% and about 24% by weight of the fired ceramic piece.

21. The method of claim 20, wherein the fired ceramic piece comprises a combined concentration of zirconium dioxide, cerium oxide, gadolinium oxide, tantalum pentoxide, and niobium pentoxide in an amount of no more than about 25% of the fired ceramic piece by volume.

22. The method of claim 21, wherein the fired ceramic piece comprises a combined concentration of zirconium dioxide, cerium oxide, gadolinium oxide, tantalum pentoxide, and niobium pentoxide in an amount of no more than about 16% of the fired ceramic piece by volume.

* * * * *